(12) United States Patent
Roldan et al.

(10) Patent No.: US 6,605,603 B1
(45) Date of Patent: Aug. 12, 2003

(54) USES OF 1-AMINO-3-(N,N-DIMETHYLAMINO)-PROPYLIDENE-1,1-BISPHOSPHONIC ACID

(75) Inventors: Emilio J. A. Roldan, Buenos Aires (AR); Anibal Perez-Lloret, Buenos Aires (AR); Guillermo Vazquez, Bahia Blanco (AR); Ricardo Boland, Bahia Blanco (AR); Sokrates E. Papapoulos, Leiden (NL)

(73) Assignees: Gador, S.A. (AR); University of Leiden (NL)

( * ) Notice: Subject to any disclaimer, the term of this patent is extended or adjusted under 35 U.S.C. 154(b) by 0 days.

(21) Appl. No.: 09/830,734
(22) PCT Filed: Oct. 29, 1999
(86) PCT No.: PCT/EP99/08269
§ 371 (c)(1),
(2), (4) Date: Jul. 27, 2001
(87) PCT Pub. No.: WO00/25794
PCT Pub. Date: May 11, 2000

(30) Foreign Application Priority Data

Oct. 30, 1998 (AR) .................................... P 98 01 05446

(51) Int. Cl.$^7$ .......................... A61K 31/66; A61K 31/04
(52) U.S. Cl. ...................... 514/103; 514/102; 514/114; 514/740
(58) Field of Search .................... 514/102, 103, 514/663, 740, 114

(56) References Cited

FOREIGN PATENT DOCUMENTS

| WO | WO 94/00129 | * | 1/1994 |
| WO | WO 97/02827 | * | 1/1997 |

* cited by examiner

*Primary Examiner*—Sreeni Padmanabhan
*Assistant Examiner*—S. Jiang
(74) *Attorney, Agent, or Firm*—Pendorf & Cutliff

(57) ABSTRACT

The present invention relates to novel uses of 1-amino-3-(N,N-dimethylamino)-propylidene-1,1-bisphosphonic acid or any of its soluble salts or any of its hydrates, in particular its use for the manufacture of a medicament for selective modulation of osteoblasts.

3 Claims, 7 Drawing Sheets

| Bisphosphonate | R1 | R2 |
|---|---|---|
| Etidronate (EHDP) | OH | $CH_3$ |
| Pamidronate (APD) | OH | $CH_2\text{-}CH_2\text{-}NH_2$ |
| Olpadronate (OPD) | OH | $CH_2\text{-}CH_2\text{-}N(CH_3)_2$ |
| $NH_2$-olpadronate ($NH_2$-OPD) | $NH_2$ | $CH_2\text{-}CH_2\text{-}N(CH_3)_2$ |

USES OF 1-AMINO-3-(N,N-DIMETHYLAMINO)-PROPYLIDENE-1,1-BISPHOSPHONIC ACID

CROSS REFERENCE TO RELATED APPLICATION

This application is a national stage of PCT/EP99/08269 filed Oct. 29, 1999, and based upon Argentina Application No. P980105446 filed Oct. 30, 1998, under the International Convention.

BACKGROUND OF THE INVENTION

The present invention relates to novel uses of 1-amino-3-(N,N-dimethylamino)-propylidene-1,1-bisphosphonic acid or any of its soluble salts or any of its hydrates.

1. Field of the Invention

The compound 1-amino-3-(N,N-dimethylamino)-propylidene-1,1-bisphosphonic acid, or any of its soluble salts or any of its hydrates, belongs to the group of bisphosphonates which are compounds containing two phosphonate groups bound to a carbon and two additional groups $R_1$ and $R_2$, respectively, which bind strongly to calcium crystals, inhibit their growth, suppress bone resorption and are being used in the treatment of a variety of disorders of bone metabolism.

2. Summary of the Invention 1-amino-3-(N,N-dimethylamino)-propylidene-1,1-bisphosphonic acid is the amino-substituted form of olpadronate (OPD) and is hereafter sometimes referred to as $NH_2$-OPD.

Bisphosphonates are recognized potent inhibitors of bone resorption and are successfully used in the treatment of common bone disorders such as osteoporosis and tumoral bone diseases, amongst others. Structurally, bisphosphonates are derivatives of methylene bisphosphonate in which the two hydrogens on the geminal carbon atom are replaced by two groups, namely $R_1$ and $R_2$, which usually are not identical. In many cases the $R_1$ moiety is a hydroxyl group, because of its ability to form a tridentate structure together with the two phosphonate groups to bind bone material.

Extensive studies have been carried out on the effects of bisphosphonates on bone cells, in particular those related to their anti-resorptive potency. The molecular mechanisms involved in such actions, however, are not clear. The anti-resorptive activity and its utility in the treatment of osteoporoses and related bone diseases have, for example, been reported and described in the following patents: WO 94/00129 to Frances M. et al., WO 93/11786 to Gueddes A. et al., WO 92/14474 to McOskar et al., U.S. Pat. No. 4,942,157 to Gall R. et al., and in U.S. Pat. No. 3,962,432 to Schmidt-Dunker M.

Although it appears that the nature of the $R_2$ moiety of bisphosphonates determines their anti-resorptive activity, replacement of the hydroxyl group in $R_1$ by an $NH_2$ group in some bisphosphonates (e.g. olpadronate and pamidronate) markedly reduces their anti-resorptive activity. This decrease in anti-resorptive efficacy of the amino derivatives is thought to be due to substitution-dependent changes in the cellular effects of the compounds, since their affinity for bone mineral is not significantly affected. This lack of anti-resorptive activity is, for example, disclosed in vanBeek et al., 1996, Journal of Bone and Mineral Research, vol. 11, no. 10, pp. 1492–1497, and international patent application PCT/EP96/02981, the latter disclosing the use of 1-amino-3-(N,N-dimethylamino)-propylidene-1,1-bisphosphonic acid for the treatment of osteoporoses, arthritis and periodontal diseases.

The structure and stability of skeletal bones is—to a high degree—influenced and determined by an equilibrium between the activities of osteoblasts and osteoclasts, i.e. the cells responsible for mineralization and resorption of bone structure, respectively. Therefore, bones are subject to a continuous restructuring process involving anabolic and catabolic reactions. In human beings, as of the age of 30, the catabolic processes prevail such that there will be a net loss in total bone substance naturally. Consequently, the rate at which the renewal of the bone tissue takes place will be lowered with increasing age.

Object of the present invention is to provide means for prevention of the onset of clinically pathological bone-conditions.

Another object of the present invention is to avoid a predisposition to bone disfunctions or bone diseases.

Yet a further object of the present invention is to optimize the physiological bone functions in patients.

The present invention in its various aspects and embodiments disclosed hereafter solves all these objectives and provides further advantages.

SUMMARY OF THE INVENTION

The present invention is related to novel uses of 1-amino-3-(N,N-dimethylamino)-propylidene-1,1-bisphosphonic acid and/or any of its soluble salts and/or any of its hydrates. For the purposes of the following specification, it is intended that the term 1-amino-3-(N,N-dimethylamino)-propylidene-1,1-bisphosphonic acid also encompasses any of its soluble salts and/or any of its hydrates.

Briefly stated, the present invention provides novel uses of 1-amino-3-(N,N-dimethylamino)-propylidene-1,1-bisphosphonic acid, medicaments comprising 1-amino-3-(N,N-dimethylamino)-propylidene-1,1-bisphosphonic acid and screening methods involving 1-amino-3-(N,N-dimethylamino)-propylidene-1,1-bisphosphonic acid.

Within one aspect of the present invention, there is provided the use of 1-amino-3-(N,N-dimethylamino)-propylidene-1,1-bisphosphonic acid for the manufacture of a medicament for selective modulation of osteoblasts. Furthermore, there is provided the use of 1-amino-3-(N,N-dimethylamino)-propylidene-1,1-bisphosphonic acid for the manufacture of a medicament for the maintenance of a healthy bone structure.

There is also provided the use of b 1-amino-3-(N,N-dimethylamino)-propylidene-1,1-bisphosphonic acid for the manufacture of a medicament for the prevention of osteopathies in healthy patients.

The invention also provides for the use of 1-amino-3-(N,N-diethylamino)-propylidene-1,1-bisphosphonic acid for the manufacture of a medicament for the treatment of patients who have recently undergone treatment with corticosteroids.

Additionally there is provided the use of 1-amino-3-(N,N-dimethylamino)-propylidene-1,1-bisphosphonic acid for the manufacture of a medicament for post-treatment of osteopathies wherein an anti-resorptive activity is not desired.

The invention also provides for the use of 1-amino-3-(N,N-dimethylamino)-propylidene-1,1-bisphosphonic acid for the manufacture of a medicament for the treatment of children having an osteopathy.

In another aspect of the invention, there is provided the use of 1-amino-3-(N,N-dimethylamino)-propylidene-1,1-bisphosphonic acid for the manufacture of a medicament for the stimulation of both signalling cascades and reaction mechanisms mediating the action of 1-amino-3-(N,N-dimethylamino)-propylidene-1,1-bisphosphonic acid which can be blocked by $Ca^{2+}$-channel blockers.

In yet another aspect of the present invention, there is provided the use of 1-amino-3-(N,N-dimethylamino)-propylidene-1,1-bisphosphonic acid for the manufacture of a medicament for the mobilization of $Ca^{2+}$-ions from $IP_3$ sensitive stores.

In yet another aspect of the invention, there is provided a method for screening for $Ca^{2+}$-channel blockers comprising the steps:

treatment of cells having $Ca^{2+}$-channels with a putative $Ca^{2+}$-channel blocker;

contacting the cells with 1-amino-3-(N,N-dimethylamino)-propylidene-1,1-bisphosphonic acid;

measuring a response as a result of the contacting step.

It is envisioned that the treatment-step and the contacting-step occur sequentially with the treatment-step preceding the contacting-step or vice versa, or that they occur simultaneously.

In another aspect, the invention also provides a method for screening for functional analogues of 1-amino-3-(N,N-dimethylamino)-propylidene-1,1-bisphosphonic acid, comprising the steps:

treatment of cells having $Ca^{2+}$-channels with $Ca^{2+}$-channel blockers;

contacting the cells with the putative functional analogue which, in the absence of any $Ca^{2+}$-channel blockers, is known to cause a $Ca^{2+}$-ion influx into the cells;

measuring a response as a result of the contacting step.

It is envisioned that the treatment-step and the contacting-step occur sequentially with the treatment-step preceding the contacting-step or vice versa, or that they occur simultaneously.

In the present invention there is also disclosed a medicament comprising 1-amino-3-(N,N-dimethylamino)-propylidene-1,1-bisphosphonic acid and at least one physiologically acceptable carrier, for the selective modulation of the osteoblasts, for the maintenance of a healthy bone structure, for the prevention of osteopathies or for the post-treatment of osteopathies where an anti-resorptive activity is not desired.

In one aspect of the present invention it provides a medicament comprising 1-amino-3-(N,N-dimethylamino)-propylidene-1,1-bisphosphonic acid, which is to be applied in healthy patients or in patients at or above 40 years of age.

The present invention also discloses a method for the selective modulation of osteoblasts and/or for the maintenance of a healthy bone structure and/or for the prevention of osteopathies in healthy patients and/or for the treatment of patients who have recently undergone treatment with corticosteroids, and/or for post-treatment of osteopathies where an anti-resorptive activity is not desired, and/or for the treatment of children having an osteopathy and/or for the stimulation of those signaling cascades and reaction mechanisms mediating the action of 1-amino-3-(N,N-diethylamino)-propylidene-1,1-bisphosphonic acid or any of its soluble salts or any of its hydrates, which can be blocked by $Ca^{2+}$-channel blockers, and/or for the mobilization of $Ca^{2+}$ ions from $IP_3$-sensitive stores, comprising administering 1-amino-3-(N,N-dimethylamino)-propylidene-1,1-bisphosphonic acid or any of its soluble salts or any of its hydrates alone or in combination with a pharmaceutical carrier to a patient, the 1-amino-3-(N,N-dimethylamino)-propylidene-1,1-bisphosphonic acid or any of its soluble salts or any of its hydrates being administered in doses of 0.1 to 1000 mg/oral application or 0.02 to 200 mg/parenteral application.

It is preferred that the term "selective modulation of osteoblasts" comprises a stimulation of the cellular activities of the osteoblasts, more preferably an influence on the $Ca^{2+}$-homeostasis of the osteoblasts. A preferred embodiment of "selective modulation" comprises a transient increase of the $Ca^{2+}$-levels in the osteoblasts. A selective modulation of osteoblasts may also encompass and manifest itself in the synthesis of osteocalcine and/or osteopontin, osteonectin, calprotectin, fibronectin, matrix Gla protein and/or bone sialoprotein.

It is intended in the present invention that the term "maintenance of a healthy bone structure" also encompass a prevention of clinically pathological conditions or diseases.

Within one aspect of the present invention it is preferred that where 1-amino-3-(N,N-dimethylamino)-propylidene-1,1-bisphosphonic acid is used for the manufacture of a medicament for the maintenance of healthy bone structure, that the medicament is applied in healthy patients, more preferably patients without osteopathies. The term "healthy bone structure" is meant to include any bone structure characterized by a balanced equilibrium between catabolic and anabolic processes resulting in a structure capable of withstanding mechanical stress that occurs as a result of the organism's activities, as well as a structure that is capable of remodelling itself by aforementioned equilibrium and repairing itself by the removal of weakened or worn-out parts and the build-up of strong parts, thereby avoiding microcracks and parts prone to fracture.

It has been found that, especially with older people, the bones have a less strong structure because of their reduced rate of renewal. Furthermore, older people may get weaker, more fragile bones due to sedentary lifestyle, muscular weakness and insufficient nutrition. As a result the affected bones, in fact, comprise "fit" mineralized structures and therefore become brittle and unstable which very often is accompanied by a tendency for fractures. These "unfit" structures have not manifested themselves yet as clinically pathological conditions but are less than ideal. They can also be found—apart from in people at or above the age of 40 years—in people recently treated with corticosteroids or in people recently treated with anti-osteoporotic agents such as fluorine and common bisphosphonates such as etidronate and chlodronate.

The term "patient" is meant to encompass human beings as well as any vertebrate animal, for example cats, dogs, cows, horses and other domestic animals.

The term "osteopathy" designates any pathological condition of the bone resulting in a weakened or irregular or abnormal bone structure. Within the present invention it is used synonymously with "bone disease". Preferably the term "osteopathy" refers to a clinically pathological condition selected from the group comprising osteoporosis, Paget's disease, arthritis, periodontal osteopenia, adolescent scoliosis, fracture, disuse osteopenia, post-transplant osteopenia, hyper-parathyroidism-associated osteopenia, drug-induced osteopenia, nutritional osteopenia, metabolic bone disease, osteopenia of prematurity and ossification disorder.

Where the term "patient" is referring to a human being, in one embodiment it is preferred that the medicament is applied in human beings at or above the age of 40 years, in another embodiment it is preferred that the medicament is applied in children. Preferably, the term "children" is meant to encompass individuals who are from 0 to 16 years old.

Where 1-amino-3-(N,N-dimethylamino)-propylidene-1, 1-bisphosphonic acid is used for the manufacture of a medicament for the prevention of osteopathies in healthy patients or for the manufacture of a medicament for the treatment of children having an osteopathy it is preferred that the osteopathy is selected from the group comprising osteoporosis, Paget's disease, arthritis, periodontal osteopenia, adolescent scoliosis, fracture, disuse osteopenia, post-transplant osteopenia, hyper-parathyroidism-associated osteopenia, drug-induced osteopenia, nutritional osteopenia, metabolic bone disease, osteopenia of prematurity and ossification disorder.

In one embodiment it is preferred that 1-amino-3-(N,N-dimethylamino)-propylidene-1,1-bisphosphonic acid—after the application of the medicament in a patient—will be present at extracellular concentrations in a range between $10^{-6}$M and $10{-}10$M, more preferably $10^{-7}$M and $10^{-9}$M, most preferably at an extracellular concentration of about $10^{-8}$M.

In the embodiment where 1-amino-3-(N,N-dimethylamino)-propylidene-1,1-bisphosphonic acid is used for the manufacture of a medicament for the stimulation of those signaling cascades and reaction mechanisms mediating the action of 1-amino-3-(N,N-methylamino)-propylidene-1,1-bisphosphonic acid, which can be blocked by $Ca^{2+}$-channel blockers it is preferred that the $Ca^{2+}$-channel blockers are selected from the group comprising nifedipine and verapamil.

In one embodiment it is preferred that 1-amino-3-(N,N-dimethylamino)-propylidene-1,1-bisphosphonic acid be used in doses of 0.01 to 1000 mg/oral application, more preferably 12.5 to 75 mg/oral application. The term "oral application" is meant to include solid or soluble liquid pharmaceutical formulations, gels, soft capsules, tablets, capsules containing solid preparations, soluble liquid forms or suspensions, and pills. Within one aspect of the present invention it is envisioned that 1-amino-3-(N,N-dimethylamino)-propylidene-1,1-bisphosphonic acid be used also for topical administration to be applied on skin and/or mucosae. Forms of application useful for this purpose comprise ointments, creams, sprays, suppositories and gels.

In another embodiment of the present invention it is preferred that 1-amino-3-(N,N-dimethylamino)-propylidene-1,1-bisphosphonic acid be used in doses of 0.02 to 200 mg/parenteral application, more preferably 2.5 to 15 mg/parenteral application. The term "parenteral application" is meant to include any application that avoids the gastrointestinal tract, for example by sub-cutaneous, intramuscular or intra-venous injection or infusion.

The term "$IP_3$-sensitive stores" refers to those intracellular stores of $Ca^{2+}$-ions which, upon the presence of $IP_3$ (=inositol triphosphate) rapidly release $Ca^{2+}$-ions. Such $IP_3$-sensitive stores encompass for example the endoplasmic reticulum and, in smooth muscle cells, the sarcoplasmic reticulum.

It is to be noted that according to the present invention the influence exerted by 1-amino-3-(N,N-dimethylamino)-propylidene-1,1-bisphosphonic acid on the $Ca^{2+}$ homeostasis of the osteoblasts, in particular an increase of the $Ca^{2+}$-levels in the osteoblasts, can occur in at least two different ways: $Ca^{2+}$-ions can be mobilized from endogenous stores, such as those which are $IP_3$-sensitive or thapsigargin-senstitive.

Secondly, there can also occur a $Ca^{2+}$-ion-influx from extracellular stores. This may for example occur through voltage-dependent $Ca^{2+}$-channels (VDCC), but other forms of $Ca^{2+}$-channels, e.g. ligand-gated channels, can be envisioned, too.

It is within the scope of the present invention that 1-amino-3-(N,N-dimethylamino)-propylidene-1,1-bisphosphonic acid also be used for screening for $Ca^{2+}$-channel blockers. The term "putative $Ca^{2+}$-channel blocker" is meant to designate a compound to be tested for its $Ca^{2+}$-channel-blocking capabilities.

The term "putative functional analogue" of 1-amino-3-(N,N-dimethylamino)-propylidene-1,1-bisphosphonic acid designates any compound that is known to cause a $Ca^{2+}$-ion influx into the cells in the absence of any $Ca^{2+}$-channel blockers and is therefore mimicking 1-amino-3-(N,N-dimethylamino)-propylidene-1,1-bisphosphonic acid in its influence on $Ca^{2+}$-homeostasis of the cells. The term "measuring a response" is also meant to include the measurement or detection of the absence of a response. Within the present invention, the term "response" is preferably meant to designate a change in cytosolic $Ca^{2+}$-levels.

It is also within the scope of the present invention to combine 1-amino-3-(N,N-dimethylamino)-propylidene-1,1-bisphosphonic acid in its novel uses together with at least one other compound/substance, in synergistic combinations. The term "combination" is meant to include the incorporation of 1-amino-3-(N,N-dimethylamino)-propylidene-1,1-bisphosphonic acid together with another (other) substance (s) into the same medicament, as well as the administering of a medicament comprising 1-amino-3-(N,N-diethylamino)-propylidene-1,1-bisphosphonic acid to a patient with another (other) substance(s), i.e. administering this (these) other substance(s) in a physically separated, i.e. spatially or temporally separated manner from the medicament. In the case where the substance(s) is (are) administered in a separated manner from the medicament comprising 1-amino-3-(N,N-dimethylamino)-propylidene-1,1-bisphosphonic acid, it is preferred that the 1-amino-3-(N,N-dimethylamino)-propylidene-1,1-bisphosphonic acid-comprising medicament is administered with the other substance(s) in a single-step (concerted intake, infusions, injections), sequential-step (one after the other) or cyclic-step fashion. In one embodiment it is preferred that the medicament comprising 1-amino-3-(N,N-dimethylamino)-propylidene-1,1-bisphosphonic acid is applied before, during or after treatment with other amino-substituted bisphosphonates. For example, a sequential administering of the 1-amino-3-(N,N-dimethylamino)-propylidene-1,-bisphosphonic acid-comprising medicament with other amino-substituted bisphosphonates may be indicated, since other amino-substituted bisphosphonates exert a partial anti-resorptive effect. So a patient may need a 1-amino-3-(N,N-dimethylamino)-propylidene-1,1-bisphosphonic acid-comprising medicament for bone formation due to the selective modulating effect of 1-amino-3-(N,N-dimethylamino)-propylidene-1,1-bisphosphonic acid on the osteoblasts, and at the same time another amino-substituted bisphosphonate for a "tunable" degree of inhibition of bone resorption, depending on his/her individual requirement.

As another example a patient might first require a high degree of inhibition of bone resorption, continue then with low or none and then change again afterwards, according to individual requirements which can be determined by biochemical, densitometrical, X-ray or other measurements performed on the bones of the individual.

Thus 1-amino-3-(N,N-dimethylamino)-propylidene-1,1-bisphosphonic acid is an ideal candidate forming the basis for an individually tunable therapy of conditions where bones are weak and/or fragile.

This substance/these substances/compounds of the aforementioned synergistic combinations is/are selected from the group comprising calcium salts, calcium citrate and calcium carbonate, other amino-substituted bisphosphonates, pharmaceutically active fluorine-containing salts, vitamins of the D-group and their metabolites, cholecalciferol, calcifediol, calcitriol, ergocalciferol, PTH, anabolic hormones, such as estrogens, substances with estrogenic activity on the bone, progestogens, androgens, growth hormones, peptides with growth hormone activity, selective modulators of the estrogenic receptor, raloxifene and others. The term "amino-substituted bisphosphonate" preferably designates a bisphosphonate compound that has an amino group at the 1-position. Other substitution positions, however, can be envisioned, too. Where the "aminoderivative" of a 1-hydroxy bisphosphonate is mentioned here, this is meant to encompass molecules having a structure in which the hydroxy-group is replaced by an amino group.

It is one of the surprising advantages of the present invention that 1-amino-3-(N,N-dimethylamino)-propylidene-1,1-bisphosphonic acid acts to avoid the formation of the aforementioned "unfit" bone structures and aids in removing them once they have been formed due to its selective modulating capabilities with respect to the osteoblasts.

Therefore, unfit mineralized structures in the bone are prevented and removed respectively. For example, these structures can arise in older people, but have not manifested themselves in clinically pathological conditions yet. Another important example where these unfit structures may occur is the growing skeleton, i.e. children. These may be healthy children or children having an osteopathy. The present invention provides means for removing these unfit structures or preventing them in the first place, thus contributing to a healthy bone structure which is capable of withstanding the mechanical stress exerted upon the bone through daily usage.

These and other aspects of the present invention will become evident upon reference to the following examples and attached figures. In addition, various references are set forth below which describe in more detail certain procedures or experimental details and are therefore incorporated by reference in their entirety.

BRIEF DESCRIPTION OF THE DRAWINGS

FIG. 1 shows the chemical structures of the R1 and R2 chains of the bisphosphonates used in the present studies, i.e. etidronate (EHDP), pamidronate (APD), olpadronate (OPD) and $NH_2$-olpadronate ($NH_2$-OPD)(=1-amino-3-(N,N-dimethylamino)-propylidene-1,1-bisphosphonic acid).

Cells were grown by 72 hours in the absence (control) or presence of the indicated concentrations of 1α, 25-dihydroxy-vitamin $D_3[1,25(OH)_2D_3]$, EHDP, APD, OPD or $NH_2$-OPD. Then osteocalcin (OC) released into the medium was quantitated as described in Example 4. Data are the average±SD of 3 independent experiments performed by triplicate.

Figure 3:
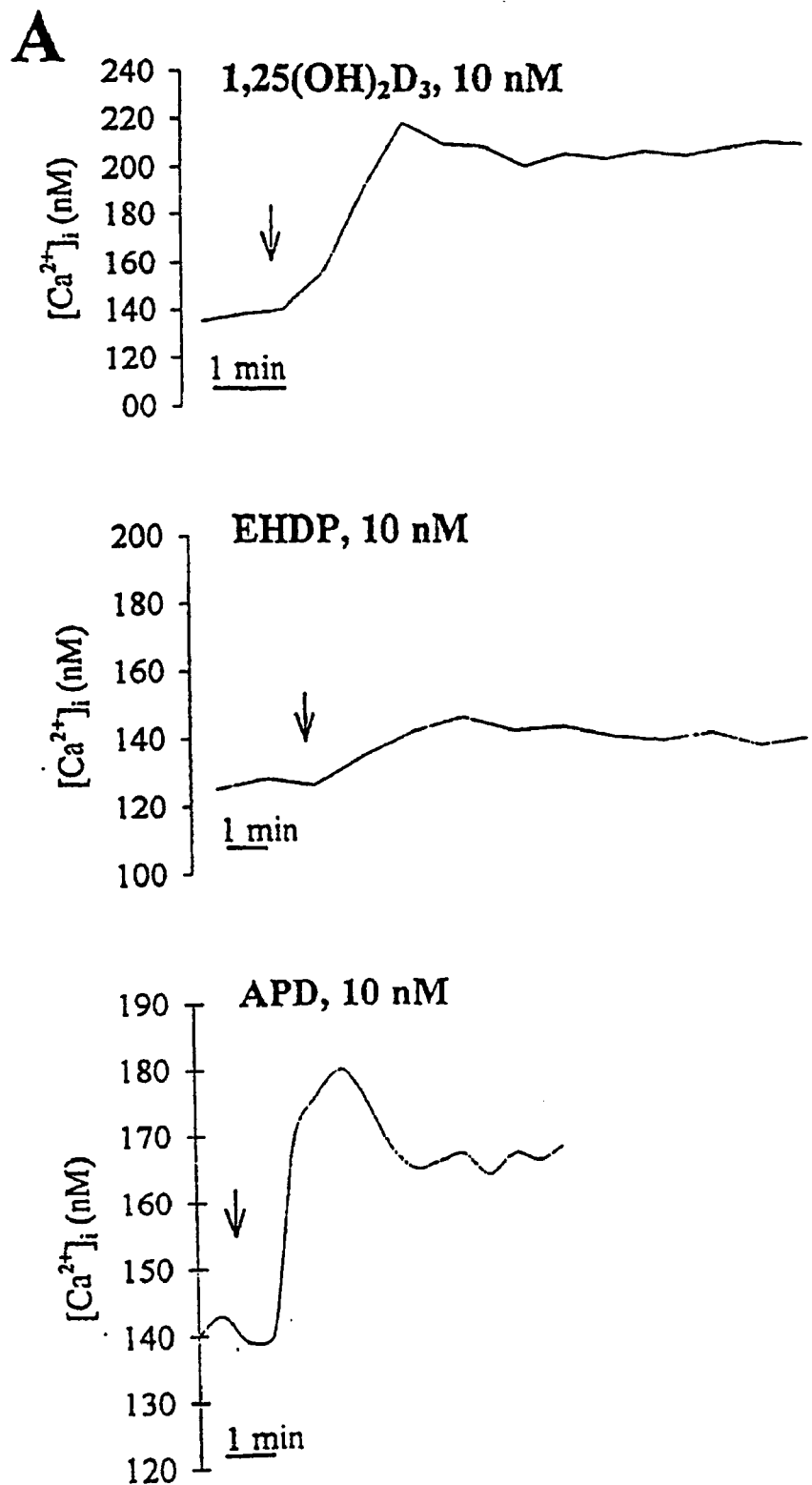
Figure 3:
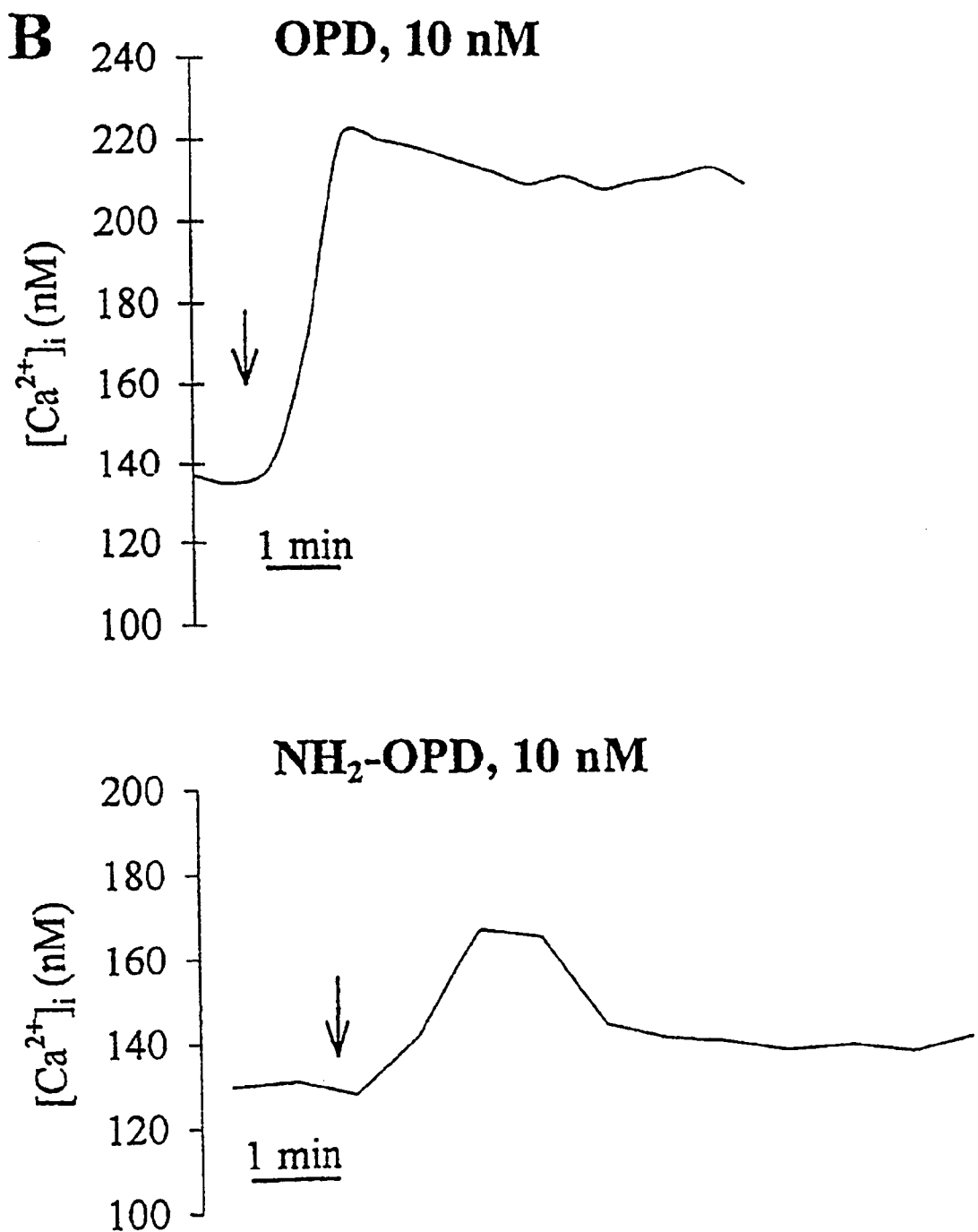

FIG. 3 shows the rapid actions of bisphosphonates on cytosolic $Ca^{2+}$ in osteoblasts:

Fura-2 loaded cells were exposed to the indicated concentrations of 1α, 25-dihydroxy-vitamin $D_3[1,25(OH)_2D_3]$, EHDP or APD (Panel A) and OPD or $NH_2$-OPD (Panel B), and cytosolic calcium levels were then monitored as described under Example 3. Shown are time-traces representative from at least 4 independent recordings.

Figure 4:
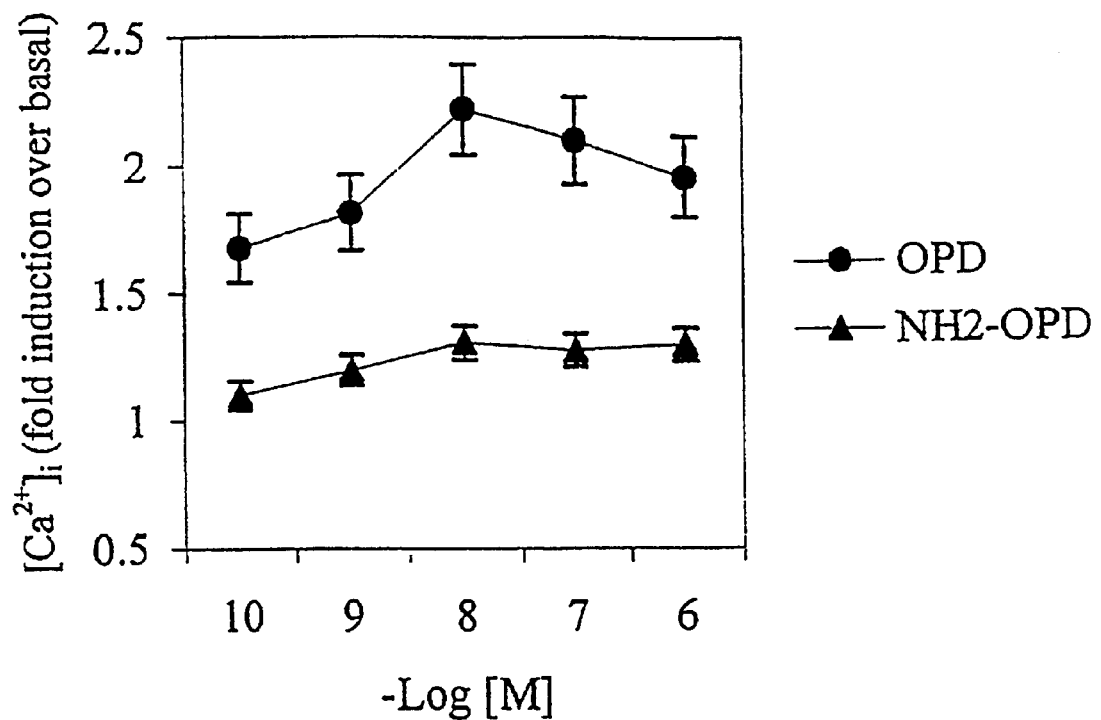

FIG. 4 shows the dose dependency of the rapid actions of OPD and $NH_2$-OPD on cytosolic $Ca^{2+}$ in osteoblasts:

Fura-2 loaded cells were treated with vehicle (buffered saline solution, Basal), or the indicated concentrations of OPD or $NH_2$-OPD, and intracellular $Ca^{2-}$ concentration ($[Ca^{2+}]_i$) was measured as described. $[Ca^{2+}]_i$ values were collected at the peak of the BP-induced $Ca^{2-}$ response. Data are the average of 4 independent $[Ca^{2+}]_i$ recordings±sd. p values (*p<0.001; **p<0.01) are given for significant differences respect to basal.

Figure 5:
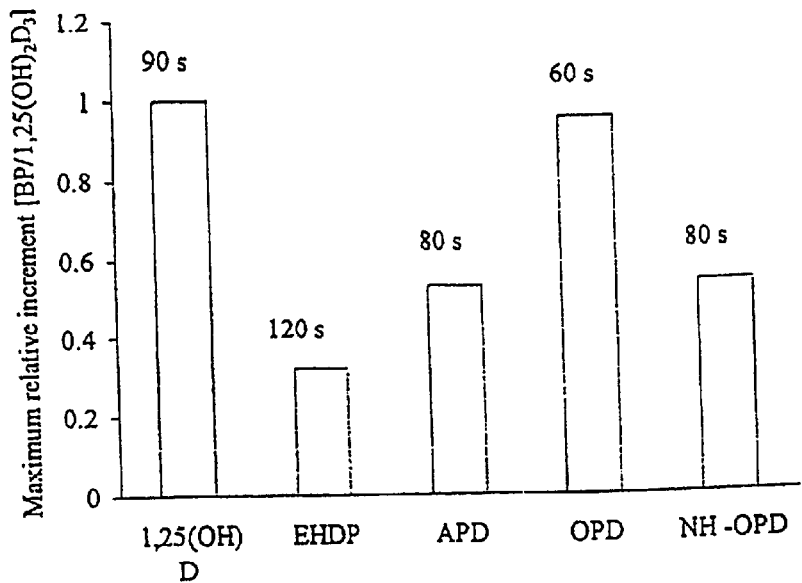
Figure 5:
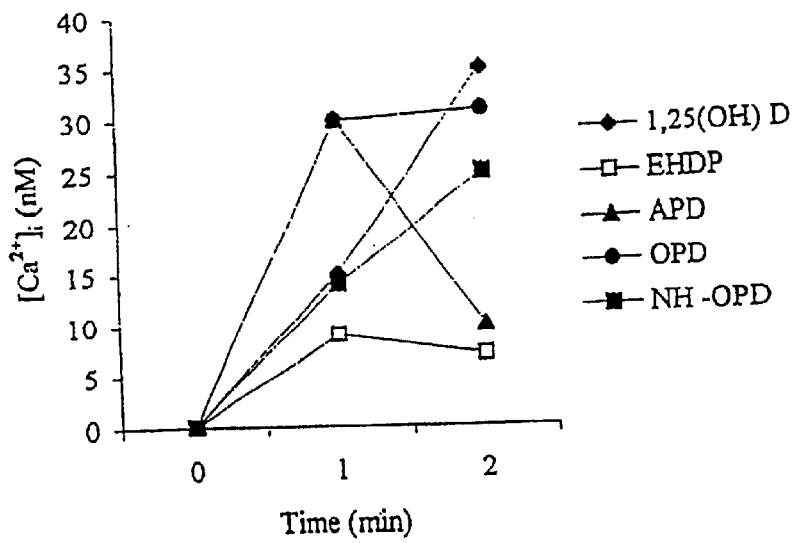

FIG. 5 shows the kinetics of the bisphosphonate-dependent cytosolic $Ca^{2+}$ change relative to $1,25(OH)_2D_3$ effect:

Fura-2 loaded cells were exposed to $1,25(OH)_2D_3$ (10 nM), or 10 nM of either EHDP, APD, OPD or $NH_2$-OPD, and cytosolic calcium was monitored, as described. A) Both the magnitude of change at maximum peak reached, as well as the corresponding time-to-peak were registered and compared to those for the steroid. Shown are results representative from 4 independent experiments. B) The early phase (0–2 min) of $Ca^{2+}_i$ increment in response to 10 nM BP or $1,25(OH)_2D3$ was monitored and plotted as change in $Ca^{2+}_i$ vs. Minutes of exposure.

Figure 6:
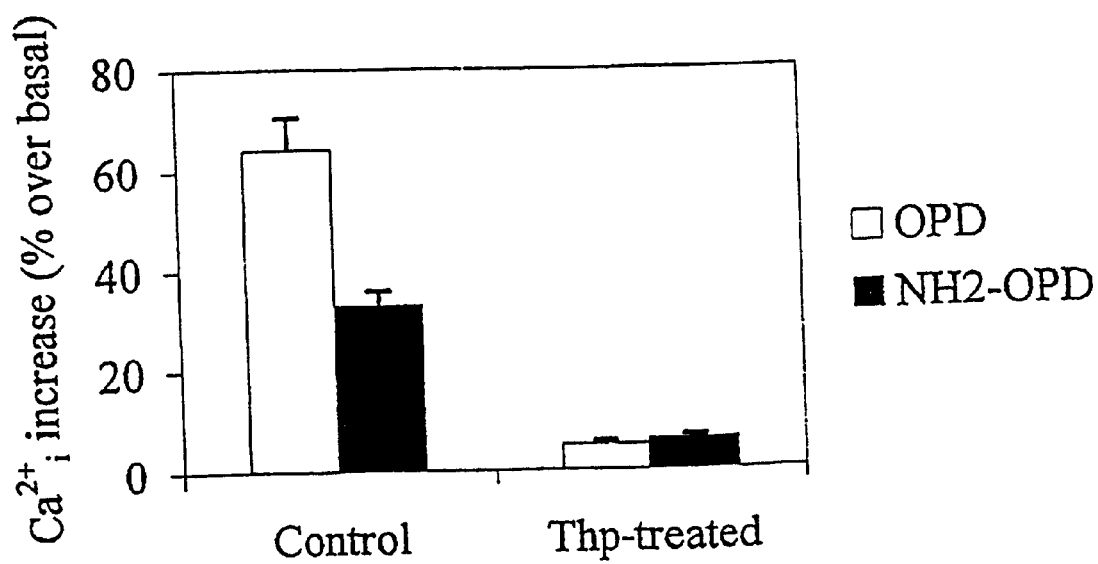

FIG. 6 shows cytosolic calcium-levels in Fura-2 loaded cells that had been treated with (Thp-treated) or without (Control) 1 μM thapsigargin and then exposed to OPD (10 nM) or $NH_2$-OPD (10 nM). Cytosolic calcium levels were monitored as described under Example 3. Shown are time-traces representative from at least 3 independent recordings.

DETAILED DESCRIPTION OF THE INVENTION

Example 1

Bisphosphonates (BP) have the following general structure:

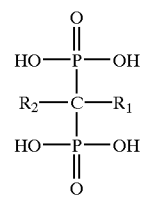

wherein $R_1$- and $R_2$-chains can have various identities. The structures of the R1 and R2 chains of the bisphosphonates used in this study are shown in FIG. 1. All of them were from Gador S.A. (Buenos Aires, Argentina). Fura-2/pentaacetoxymethyl ester (Fura-2/AM), pluronic F-127, nifedipine, verapamil, neomycin, Dulbecco's modified Eagle's medium and fetal bovine serum were from Sigma Chemical Co. (St.Louis, Mo., USA). U73122 (1-(6-((17β-3-methoxyestra-1,3,5(10)-trien-17-yl)amino)hexyl)-1H-pyrrole-2,5-dione) and U73343 (1-(6-((17β-3-methoxyestra-1,3,5(10)-trien-17-yl)amino)hexyl)-2,5-pyrrolidine) were from Biomol Research Laboratories Inc. (Plymouth Meeting, Pa., USA). All other reagents used were of analytical grade.

Example 2

Cell Culture

Osteoblast-like rat osteosarcoma cells (ROS17/2.8) were cultured as monolayers at 37° C. in Dulbecco's modified Eagle's medium (DME) containing 10% fetal bovine serum under humidified air (5.5% $CO_2$). After 48 hours, medium was changed to DME containing 1% fetal bovine serum. Unless otherwise stated, cells were allowed to grow until confluence (4–5 days after plating).

Example 3

Intracellular Calcium Measurements

Intracellular $Ca^{2+}$ changes were monitored by using the $Ca^{2+}$-sensitive fluorescent dye Fura-2 as previously described (Vasquez et al., 1998, J. Biol. Chem. 273, 33954–33960). Cell dye loading was achieved by incubating the cells in buffer A containing (in mM): 138 NaCl, 5 KCl, 1 $MgCl_2$, 5 glucose, 10 HEPES (pH 7.4), 1.5 $CaCl_2$, plus 0.1% bovine serumalbumin (BSA), 2 $\mu$M of the pentaacetoxymethylester derivative (membrane permeable) Fura-2/AM and 0.012% pluronic F-127, in the dark during 40 min at room temperature (20–25° C.) in order to minimize dye compartmentalization. Unloaded dye was washed out and cells were stored in buffer B (buffer A without BSA, Fura-2/AM and pluronic F-127) in the dark (room temperature) by at least 30 min prior to use, to allow for complete intracellular dye deesterification. For fluorescence measurements the coverslips containing dye-loaded cells were mounted into quartz cuvettes and introduced into the thermostatized (37° C.) sample compartment of a SLM Aminco 8100 spectrofluorimeter. Fura-2 intracellular fluorescence intensity was monitored at an emission wavelength of 510 nm (8 nm bandpass) by alternating with an electronically controlled chopper (300 Hz) the excitation wavelength between 340 and 390 nm employing a dual excitation monochromator at 4 nm bandpass. Signals from short and long wavelength were ratioed (R=340/390) thus making the measurement independent of variations in cellular dye content, dye leakage or photobleaching. Calibration of Fura-2 signal to calculate $[Ca^{2+}]_i$ values was performed for each coverslip as follows: maximal (Rmax) and minimal (Rmin) intracellular dye fluorescence signals were determined by adding 5 $\mu$M ionomycin plus 3 mM $Ca^{2+}$ and 10 mM EGTA (pH 7.0) plus 10 mM Tris-base (pH 9.0), respectively. Under these conditions of measurement (37° C., cytosolic environment for the dye), the dissociation constant (Kd) for the $Ca^{2+}$-Fura-2 complex is generally assumed to be 225 nM (13), and $[Ca^{2+}]_i$ derives from:

$$[Ca^{2+}]_i = Kd(R-Rmin)/(Rmax-R) \times \beta$$

where R is the ratio of Fura-2 fluorescence at the selected wavelengths, Rmax and Rmin represent ratios from $Ca^{2+}$ saturated and $Ca^{2+}$ free intracellular dye, respectively, and $\beta$ is the ratio between the specific fluorescence of the $Ca^{2+}$ free and $Ca^{2+}$ bound forms of the dye at the longer wavelength ($Sf_2/Sb_2$).

Example 4

Determination of Osteocalcin Synthesis

Osteoblasts grown by 48 hours in multiwells were changed to Dulbecco's modified Eagle's medium containing 1% fetal bovine serum plus the indicated concentration of BP, $10^{-8}$ M 1,25$(OH)_2D_3$ (positive control), or vehicle alone, and then allowed to grow for an additional period of 72 hours. The medium from each well was collected and stored frozen at −80° C. until use for osteocalcin measurements. Osteocalcin (OC) was quantitatively measured by radio-immunoassay using a commercially avalaible kit (Osteocalcin DSL-6900, Diagnostic Systems Laboratories Inc., Webster, Tex., USA) according to manufacturer's instructions. Osteocalcin values were corrected for total cellular protein content.

Example 5

Statistical Analysis

Statistical significance of data was evaluated using Student's t-test (14) and probability values below 0.05 (p<0.05) were considered significant. Quantitative data are expressed as means±standard deviation (sd) from the indicated set of experiments Example 6

Synthesis and release of the bone matrix protein osteocalcin in response to the action of olpadronate and $NH_2$-OPD.

Figure 2:
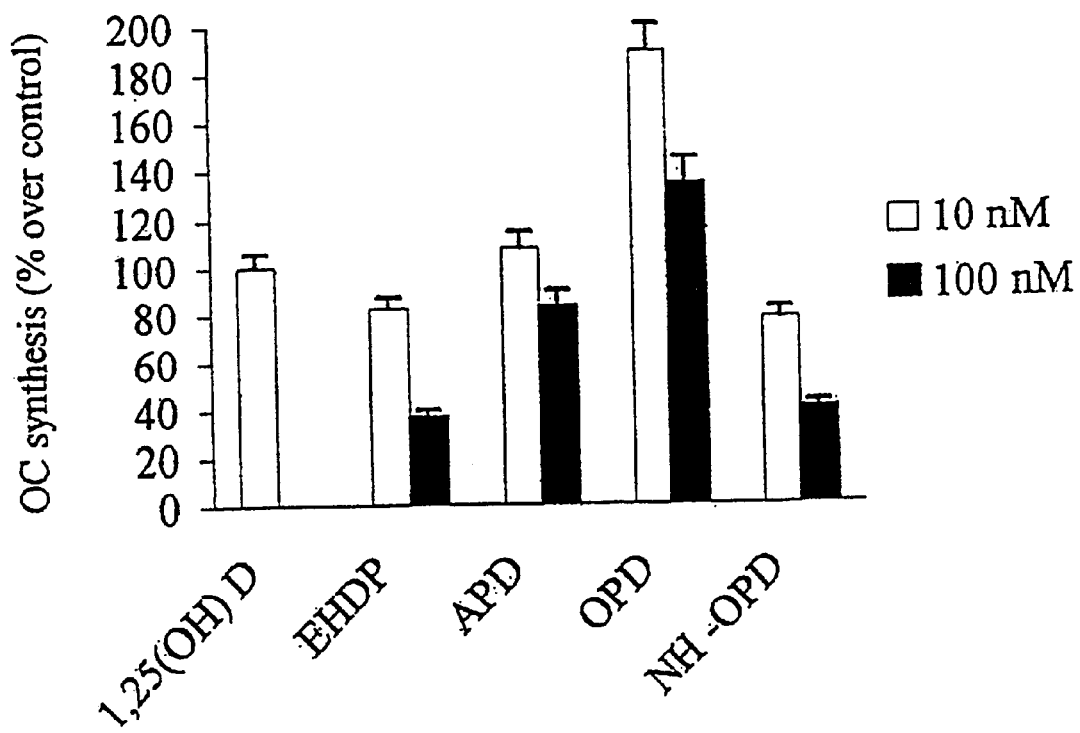
FIG. 2 shows the induction of osteocalcin (OC) synthesis by bisphosphonates in cultured osteoblasts.

We first examined the action of both olpadronate (OPD) and $NH_2$-OPD (see FIG. 1 for chemical structures) on the synthesis and release of the bone matrix protein osteocalcin (OC), and compared it with that of the bisphosphonates pamidronate (APD) and etidronate (EHDP), both being shown in FIG. 1. In osteoblasts incubated during 72 hours in the presence of $10^{-8}$ M 1,25$(OH)_2D_3$, release of OC into the culture medium was increased 100% respect to control, untreated cells (FIG. 2). Under the same incubating conditions OPD and $NH_2$-OPD markedly stimulated OC synthesis in a dose-dependent fashion, as EHDP and APD did. Both APD and OPD were more effective than the steroid hormone whereas the action of $NH_2$-OPD was lower than for the secosteroid, being comparable to EHDP. At $10^{-8}$ M, the order of potency relative to 1,25$(OH)_2D_3$ was: OPD (1.9)>APD(1.1)>1,25$(OH)_2D_3$(1.0)>EHDP=$NH_2$-OPD(0.85). At $10^{-7}$ M the induction of OC synthesis was significantly reduced, but the order of potency among the bisphosphonates remained the same. No significant differences with respect to basal OC synthesis was detected when cells were exposed to concentrations of BPs below $10^{-8}$ M. In order to determine the possibility that, as for other anabolic parameters, short term alterations of intracellular $Ca^{2+}$ regulation could be related to the action of these bisphosphonates on OC induction, we used fluorimetry to monitor changes in osteoblast $Ca^{2+}_i$ levels. The secosteroid 1,25$(OH)_2D_3$ acts as a $Ca^{2+}$ mobilizing hormone in rat osteoblasts, its response being well documented and characterized in Farach-Carson et al., 1998, Am.J.Kidney Dis. 31, 729–742. Thus, the steroid also represents a good positive reference for evaluation of BP effects on $Ca^{2+}_i$ in these cells. In Fura-2 loaded cells, similarly to 1,25$(OH)_2D_3$, EHDP, APD and OPD induced a rapid (30–60 sec) and sustained (>5 min) increase in $[Ca^{2+}]_i$ with a biphasic time-course profile, suggesting contribution by both release of $Ca^{2+}$ from endogenous stores and cation influx from the outside (FIG. 3). $NH_2$-OPD, generated a rapid (60 sec) but transient $Ca^{2+}$ rise, with a marked down-turn phase after peak returning to near basal levels within 1–2 min (FIG. 3B). For OPD and its aminoderivative, increments in $[Ca^{2+}]_i$ become detectable from 10–10 M (1.1–1.2 fold over basal levels, p<0.05), but maximal differences with respect to basal were reached at $10^{-8}$ M (1.4–1.6 fold stimulation, p<0.01; FIG. 4). Maximal changes in cytosolic $Ca^{2+}$ relative to 1,25$(OH)_2D_3$ showed that only OPD was equipotent to the steroid (FIG. 5A) with a time-to-peak significantly shorter than that for the hormone (60 vs. 90 seconds, for OPD vs. 1,25$(OH)_2D_3$, respectively). EHDP, APD and $NH_2$-OPD were less effective than the steroid to increase intracellular $Ca^{2+}$. However, both APD and $NH_2$-OPD showed time-to-peak values comparable to that of the hormone (80 vs. 90 seconds, for either APD and $NH_2$-OPD vs. $1,25(OH)_2D_3$, respectively) whereas EHDP exhibited a highly delayed kinetics (time-to-peak= 120 seconds). The kinetic analysis of the initial phase of $Ca^{2+}$ rise induced by these compounds revealed that, as noted above, EHDP exhibited the slowest rate of $Ca^{2+}$ elevation (FIG. 5B).

In ROS17/2.8 cells the rapid, non-genomic $Ca^{2+}{}_i$ response to $1,25(OH)_2D_3$ is composed of an initial fast sterol-induced $Ca^{2+}$ release from endogenous thapsigargin-sensitive stores which is followed by cation influx from the outside (see Khoury et al., 1995, J.Nutr. 125, 1699S–1703S). This cation entry pathway accounts for the sustained $Ca^{2+}{}_i$ phase, which has been shown to be contributed by L-type voltage-dependent (VDCC) $Ca^{2+}$ channels. As $NH_2$-OPD has been shown to be absolutely devoid of antiresorptive properties (Van Beek E. et al., 1996, J. Bone Miner. Res. 11, 1492–1497), particularly at doses at which, according to the present invention, some cellular effects on both osteocytes and osteoblasts are preserved it is here proposed to be a selective modulator of the osteoblast. Thus, our attention was focused on OPD and its amino-substituted analog and experiments were performed to determine if similar $Ca^{2+}$ routes were involved in the effect of these compounds on $[Ca^{2+}]_i$ reported here. As for the steroid, pretreating the cells with the VDCC blockers nifedipine (2 $\mu$M) or verapamil (5 $\mu$M) only partially (70%) reduced the $[Ca^{2+}]_i$ increase induced by OPD, but almost completely abolished the action of $NH_2$-OPD (see Example 7). In the case of OPD, the effect of VDCC blockade was particularly evident at the influx phase of the response, while the early $Ca^{2+}{}_i$ transient remained unaltered (not shown). In order to evaluate if the fast, early phase of $Ca^{2+}$ increase by BPs involves activation of the phosphoinositide-specific phospholipase C (PLC) pathway, the action of two structurally and mechanistically unrelated enzyme inhibitors on BP-induced early $Ca^{2+}$ response was assayed. The rapid (1 min) OPD- and $NH_2$-OPD-dependent increase in cytosolic $Ca^{2+}$ was totally blocked by pretreatment with the PLC inhibitors U73122 (2 $\mu$M) or neomycin (0.5 mM) (see Example 8) but not by U73343 (not shown), an analogue of U73122 devoid of effect on PLC (Vazquez G. et al., 1998, J. Biol. Chem. 273, 33954–33960).

When intracellular muscle $Ca^{2+}$ stores were pharmacologically depleted by inhibition of the sarcoplasmic reticulum $Ca^{2+}$-ATPase with 1 $\mu$M thapsigargin, the response to either OPD or $NH_2$-OPD, was completely blocked (FIG. 6).

Example 7

Effects of Nifedipine and Verapamil on the $Ca^{2+}$ Response of Osteoblasts to OPD and $NH_2$-OPD Fura-2 loaded osteoblasts were treated with vehicle (buffered saline solution, Basal), OPD (10–8 M) or $NH_2$-OPD ($10^{-8}$ M) and intracellular $Ca^{2+}$ concentration ($[Ca^{2+}]_i$) was measured as described. Given are $[Ca^{2+}]_i$ values corresponding to the plateau phase (5 min after BP exposure; see FIG. 3) of the BP-induced $Ca^{2+}$ response. When used, both nifedipine (2 $\mu$M) and verapamil (5 $\mu$M) were added 3 min before stimulation. Data are the average of 5 independent $[Ca^{2-}]_i$ recordings±sd. p values (*p<0.001; **p<0.01) are given for significant differences respect to basal. Percent (%) inhibition refers to the decrease in $\Delta[Ca^{2+}]_i$.

TABLE 1

Effects of nifedipine and verapamil on the $Ca^{2+}$ response of osteoblasts to OPD and $NH_2$-OPD

|  | $[Ca^{2+}]i$ (nM) | $\Delta[Ca^{2+}]i$ | % Inhibition |
|---|---|---|---|
| Basal | 135 ± 6 |  |  |
| OPD | 205 ± 10* | 70 |  |
| $NH_2$-OPD | 150 ± 3** | 15 |  |
| Nifedipine pretreatment: |  |  |  |
| OPD | 156 ± 8** | 21 | 70 |
| $NH_2$-OPD | 137 ± 6 | 2 | 90 |
| Verapamil pretreatment: |  |  |  |
| OPD | 146 ± 5 | 11 | 85 |
| $NH_2$-OPD | 133 ± 7 | — | 100 |

Example 8

Effects of Phospholipase C Inhibition on OPD and $NH_2$-OPD Induced $Ca^{2+}{}_i$ Responses in Osteoblastic Cells.

Fura-2 loaded cells were treated with vehicle (buffered saline solution, Basal), OPD ($10^{-8}$ M) or $NH_2$-OPD ($10^{-8}$ M) and intracellular $Ca^{2+}$ concentration ($[Ca^{2+}]_i$) was measured as described. Unless otherwise indicated, $[Ca^{2+}]_i$ stimulation was evaluated at the plateau phase of the BP-induced response (see FIG. 3). When used, the PLC inhibitors U73122 (2 $\mu$M) or neomycin (0.5 mM, data in parentheses) were added into the measurement cuvette 3 min before stimulation. In the PLC-inhibition assay $[Ca^{2+}]_i$ values measured at 1- and 5-min. after stimulation are given. Results are expressed as percent of control (100%) to allow comparison among different assay conditions, and are the average of 3 independent experiments±sd. *p<0.001; **p<0.01. Percent (%) inhibition refers to the decrease in $\Delta[Ca^{2+}]_i$.

TABLE II

Effects of phospholipase C inhibition on OPD and $NH_2$-OPD induced $Ca^{2+}{}_i$ responses in osteoblastic cells.

|  | $[Ca^{2+}]i$ | $\Delta[Ca^{2+}]i$ | % Inhibition |
|---|---|---|---|
| Control | 100 | — |  |
| OPD | 164 ± 9* | 64 |  |
| $NH_2$-OPD | 137 ± 3** | 37 |  |
| U73122 (or neomycin + OPD: |  |  |  |
| 1 min | 105 ± 3(98 ± 2) | — | 100(100) |
| 5 min | 100 ± 5(100 ± 8) | — | 100(100) |
| U73122 (or neomycin + $NH_2$-OPD: |  |  |  |
| 1 min | 101 ± 5(99 ± 1) | — | 100(99) |
| 5 min | 100 ± 11(100 ± 5) | — | 100(100) |

Example 9

The present in vitro studies were conducted in order to evaluate the effects of the olpadronate and its analog $NH_2$-OPD on intracellular $Ca^{2+}$ levels in cultured osteoblasts. It is well documented that replacing the —OH group at R1 in BP with a —$NH_2$ group induces deep changes in the biological properties of the BP, the magnitude of which depends on the nature of the parental molecule. Indeed, replacement of the hydroxyl group of etidronate by an amino group produces no detectable effect on antiresorptive efficacy of this compound, whereas the equivalent substitution in OPD leads to complete loss of antiresorptive activity (see van Beek E. et al., 1996, J. Bone Miner. Res. 11, 1492–1497).

The observed profile for OPD $Ca^{2+}_i$ response was highly similar to that of $1,25(OH)_2D_3$, involving an initial rapid BP-induced $Ca^{2+}$ mobilization from thapsigargin-sensitive endogenous stores, followed by cation influx from the extracellular millieu which finally accounts for the sustained $Ca^{2+}_i$ phase. The concept that, similarly to $1,25(OH)_2D_3$, the rapid BP-induced $Ca^{2+}_i$ transient is due to mobilization of the cation from $IP_3$-sensitive stores, is strongly supported by the blocking effect of the PLC inhibitors U73122 and neomycin, both acting at different sites of PLC activity. In ROS17/2.8 cells, $1,25(OH)_2D_3$ induces a fast (30–60 seconds) and monophasic generation of $IP_3$ (see Lieberherr, M., 1987, J. Biol. Chem. 262, 13168–13173; Civitelli et al., 1990, Endocrinology 127, 2253–2262). Although the present data suggest that a similar mechanism of endogenous $Ca^{2+}$ mobilization might operate for these two related BPs, the effects of both OPD and $NH_2$-OPD on phospholipid metabolism in these cells remains to be investigated. As polyphosphoinositide turnover could be directly or indirectly involved in the control of $Ca^{2+}$ influx from outside the cell (see Irvine, RF., 1992, FASEB J. 6, 3085–3091), it appears that differences in the extent of inositol phosphate liberation account for the greater stimulation of $Ca^{2+}$ entry through $Ca^{2+}$ channels by OPD and $NH_2$-OPD here reported.

We observed that the $Ca^{2+}$ influx phase of the $Ca^{2+}$ response to OPD and $NH_2$-OPD was, although at different extent, abolished by VDCC blockers, suggesting that modulation of voltage-dependent $Ca^{2+}$ channels is involved in the non-genomic action of both BPs in osteoblastic cells.

The events by which BPs exert genomic (e.g., induction of OC synthesis) and non-genomic (e.g., rapid activation of the calcium message) actions are certainly both temporally and, probably, spatially separated during physiological bone remodeling. Many studies, particularly those relating membrane-initiated and nuclear receptor-mediated pathways in $1,25(OH)_2D_3$ actions on bone, have clearly established that the induction of the $Ca^{2+}$ signal is not always necessary for activation of the nuclear processes in osteoblasts (see Khoury et al., 1994, Endocrinology 135, 2446–2453). However, $Ca^{2+}$ signals have systematically been associated with changes in the expression level of osteocalcin and osteopontin (see Farach-Carson et al., Am. J. Kidney Dis. 31, 729–742, and those references therein). We observed here that $NH_2$-OPD exhibits a diminished efficacy relative to that of the parental molecule OPD to induce OC synthesis, whereas the magnitude of changes in cytosolic $Ca^{2+}$ are also significantly lower in response to $NH_2$-OPD than for OPD, with highly different profiles.

Thus, it suggests the existence of a direct correlation between BP potency to induce OC synthesis and their ability to generate rapid changes in cytosolic $Ca^{2+}$. This observation is valid for all of the other BPs assayed in the present studies. On this basis, it seems as for the secosteroid hormone $1,25(OH)_2D_3$, the rapid, non-genomic actions of BPs on the osteoblast $Ca^{2+}$ signalling system could trigger the BP genomic effect, thus affecting osteogenesis. Although the structural change introduced in OPD could be altering its interaction with its cellular target/s, the observed differences between OPD and $NH_2$-OPD action on $Ca^{2+}$ regulation could be related to differential signalling cascades and/or mechanisms mediating the action of each of these BPs. At the doses used in the present study $NH_2$-OPD has been shown to act as a selective modulator of the osteoblast. The possibility then rises that the differential effects of OPD and $NH_2$-OPD on the $Ca^{2+}$ homeostasis of the osteoblast could explain their differences in antiresorptive potency. These results show that $NH_2$-OPD is a selective modulator of the osteoblast, particularly in the above-mentioned novel uses.

The inventive features disclosed in the preceding description as well as in the claims, tables and figures can be essential to the realization of the invention in its various embodiments, either singly or in the form of random combinations.

What is claimed is:

1. A method for stimulation of the cellular activities of osteoblasts, said method consisting of administering to a patient an osteblast stimulating effective amount of a pharmaceutical composition consisting of 1-amino-3-(N,N-dimethylamino)-propylidene-1,1-bisphosphonic acid, any of its pharmaceutical acceptable soluble salts or any of its pharmaceutical acceptable hydrates as an active agent.

2. A method for stimulation of the cellular activities of osteoblasts for influencing a $Ca^{2-}$-homeostasis of the osteoblasts, said method consisting of: administering to a patient an osteoblast stimulating effective amount of a pharmaceutical composition consisting of 1-amino-3-(N,N-dimethylamino)-propylidene-1,1-bisphosphonic acid, any of its pharmaceutical acceptable soluble salts or any of its pharmaceutical acceptable hydrates as an active agent.

3. A method for stimulation of the cellular activities of osteoblasts for inducing a transient increase of the $Ca^{2+}$-levels in the osteoblasts, said method consisting of: administering to a patient an osteoblast stimulating effective amount of a pharmaceutical composition consisting of 1-amino-3-(N,N-dimethylamino)-propylidene-1,1-bisphosphonic acid, any of its pharmaceutical acceptable soluble salts or any of its pharmaceutical acceptable hydrates as an active agent.

* * * * *